United States Patent [19]

Athanasiou et al.

[11] Patent Number: 5,433,215
[45] Date of Patent: Jul. 18, 1995

[54] ARTHROSCOPIC INDENTER

[75] Inventors: Kyriacos Athanasiou, Helotes; George Constantinides, San Antonio, both of Tex.

[73] Assignee: Board of Regents, University of Texas System, Austin, Tex.

[21] Appl. No.: 113,729

[22] Filed: Aug. 27, 1993

Related U.S. Application Data

[63] Continuation of Ser. No. 871,523, Apr. 21, 1992, abandoned.

[51] Int. Cl.$^6$ .................................................. A61B 5/103
[52] U.S. Cl. ........................................ 128/774; 73/81; 364/413.02; 364/506
[58] Field of Search ............... 128/774, 695, 645, 652, 128/4, 6; 73/78, 79, 81, 83, 85, 573; 364/413.02, 506, 508

[56] References Cited

U.S. PATENT DOCUMENTS

| | | | |
|---|---|---|---|
| 4,132,224 | 1/1979 | Randolph | 73/81 |
| 4,159,640 | 7/1979 | Leveque et al. | 73/81 |
| 4,253,467 | 3/1981 | Frazier | 128/630 |
| 4,364,399 | 12/1982 | Dashefsky | 128/774 |
| 4,414,962 | 11/1983 | Carson | 128/6 |
| 4,461,281 | 7/1984 | Carson | 128/3 |
| 4,503,865 | 3/1985 | Shishido | 128/774 |
| 4,756,304 | 7/1988 | Watanabe | 128/6 |
| 4,848,141 | 7/1989 | Oliver et al. | 73/81 |
| 4,888,490 | 12/1989 | Bass et al. | 250/561 |
| 4,896,339 | 1/1990 | Fukumoto | 377/19 |
| 5,003,982 | 4/1991 | Halperin | 128/695 |
| 5,067,346 | 11/1991 | Field | 73/81 |
| 5,146,779 | 9/1992 | Sugimoto et al. | 73/81 |

OTHER PUBLICATIONS

Mow, et al., "Biphasic Indentation of Articular Cartilage-II. A Numerical Algorithm and an Experimental Study", *J. Biom.*, vol. 22, pp. 853-861, 1989.
Mow, et al., "Biphasic Creep and Stress Relaxation of Articular Cartilage in Compression: Theory and Experiments", *J. Biom*, vol. 102, pp. 73-83, 1980.

*Primary Examiner*—Stephen C. Pellegrino
*Assistant Examiner*—Guy V. Tucker
*Attorney, Agent, or Firm*—Greenlee and Winner

[57] ABSTRACT

An arthroscopic indenter for measuring creep deformation behavior, stress relaxation behavior and thickness of cartilage in vivo and in situ. A computer-based system measures deformation or force information upon cartilage and processes that information for closed-loop control of an indenter tip while also calculating intrinsic properties associated with the cartilage such as stiffness, compressibility and/or permeability.

11 Claims, 10 Drawing Sheets

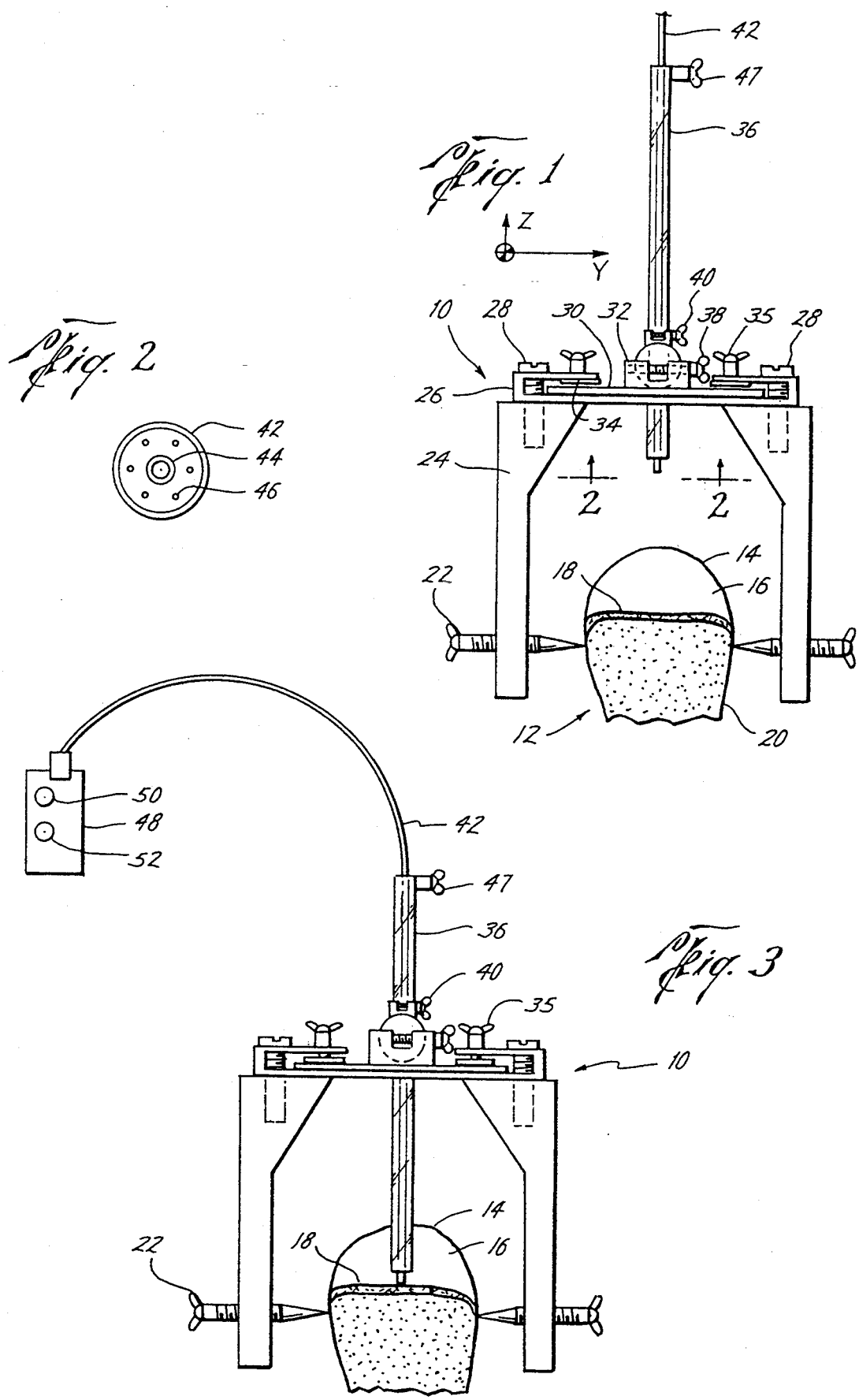

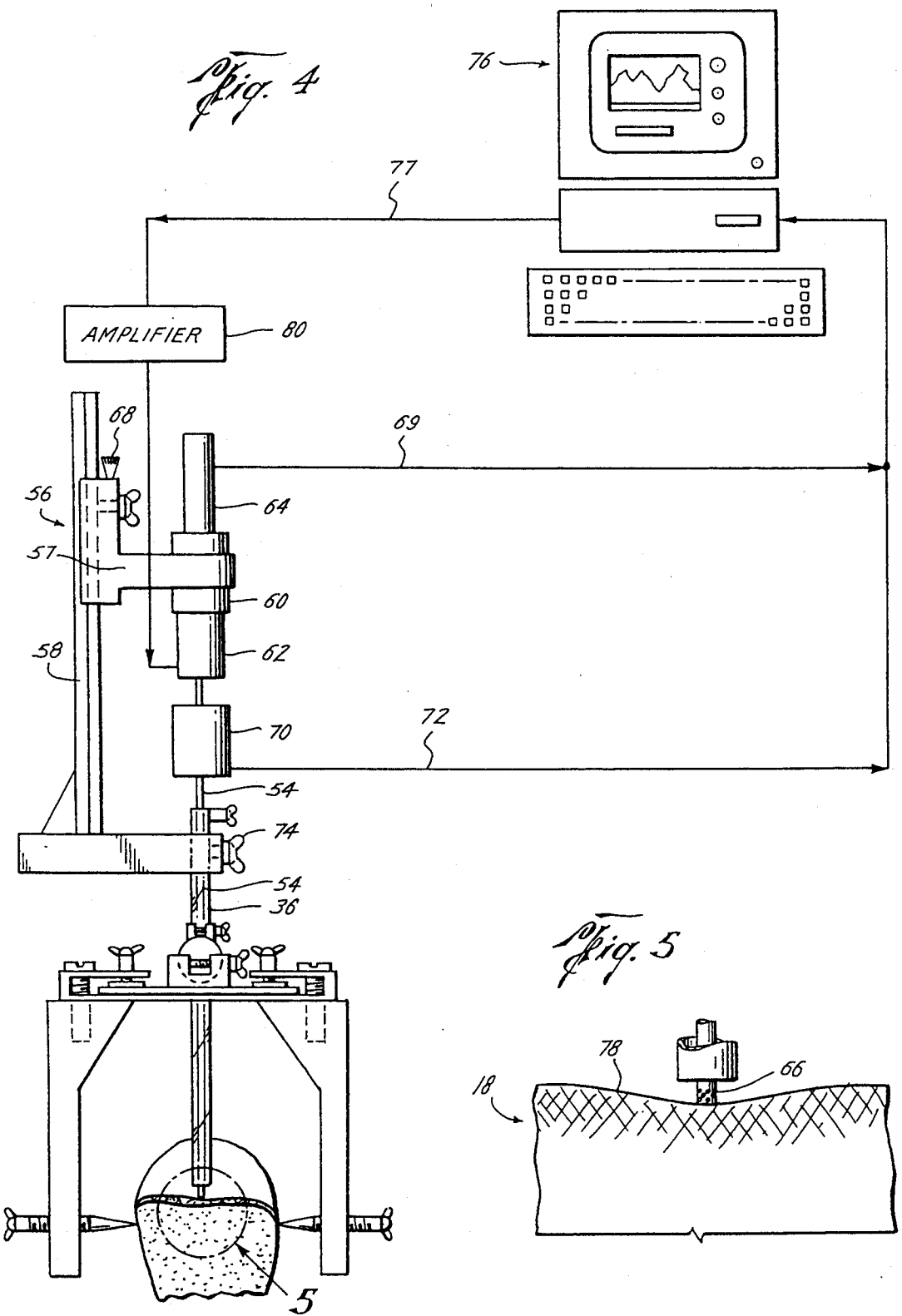

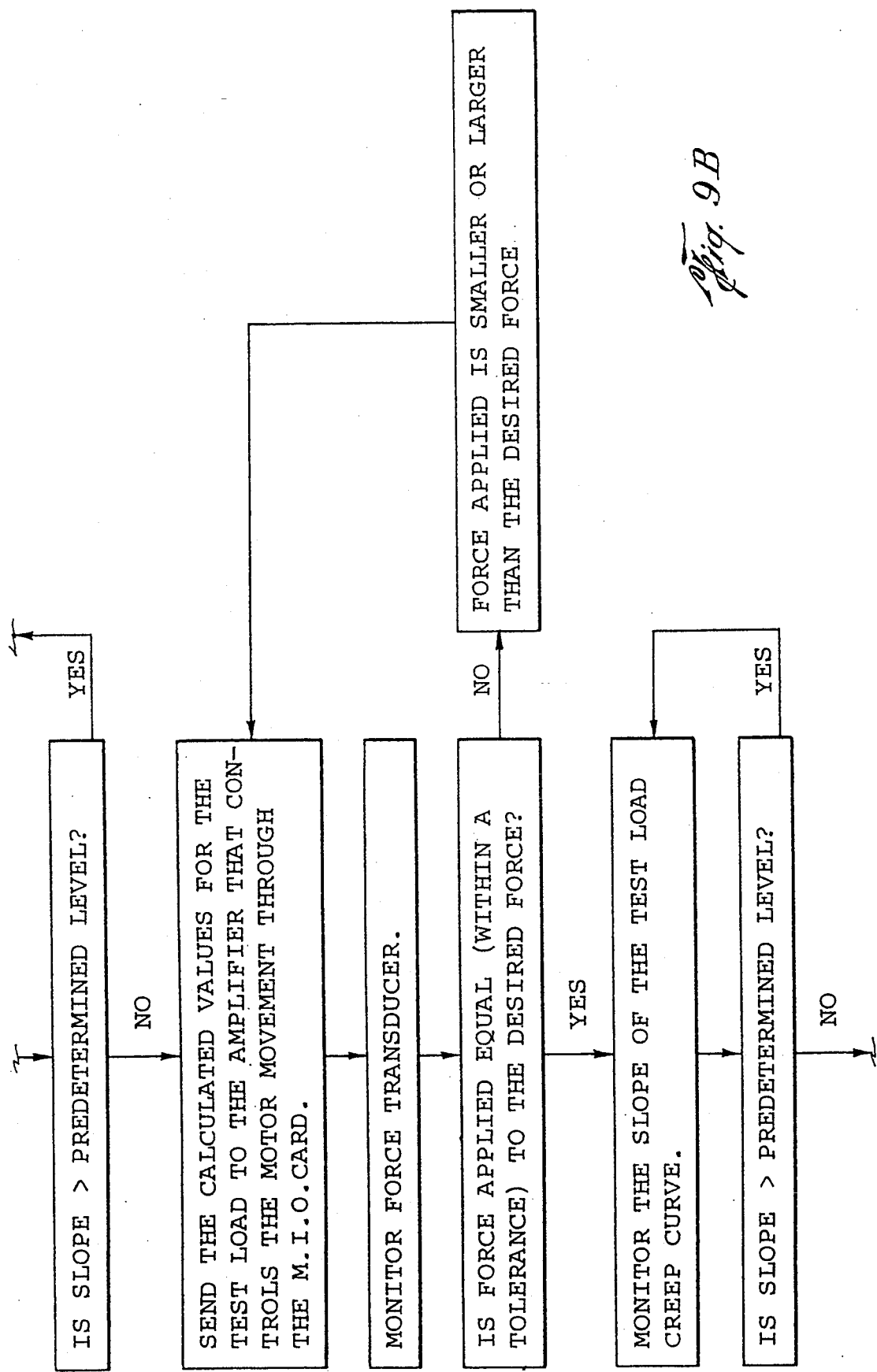

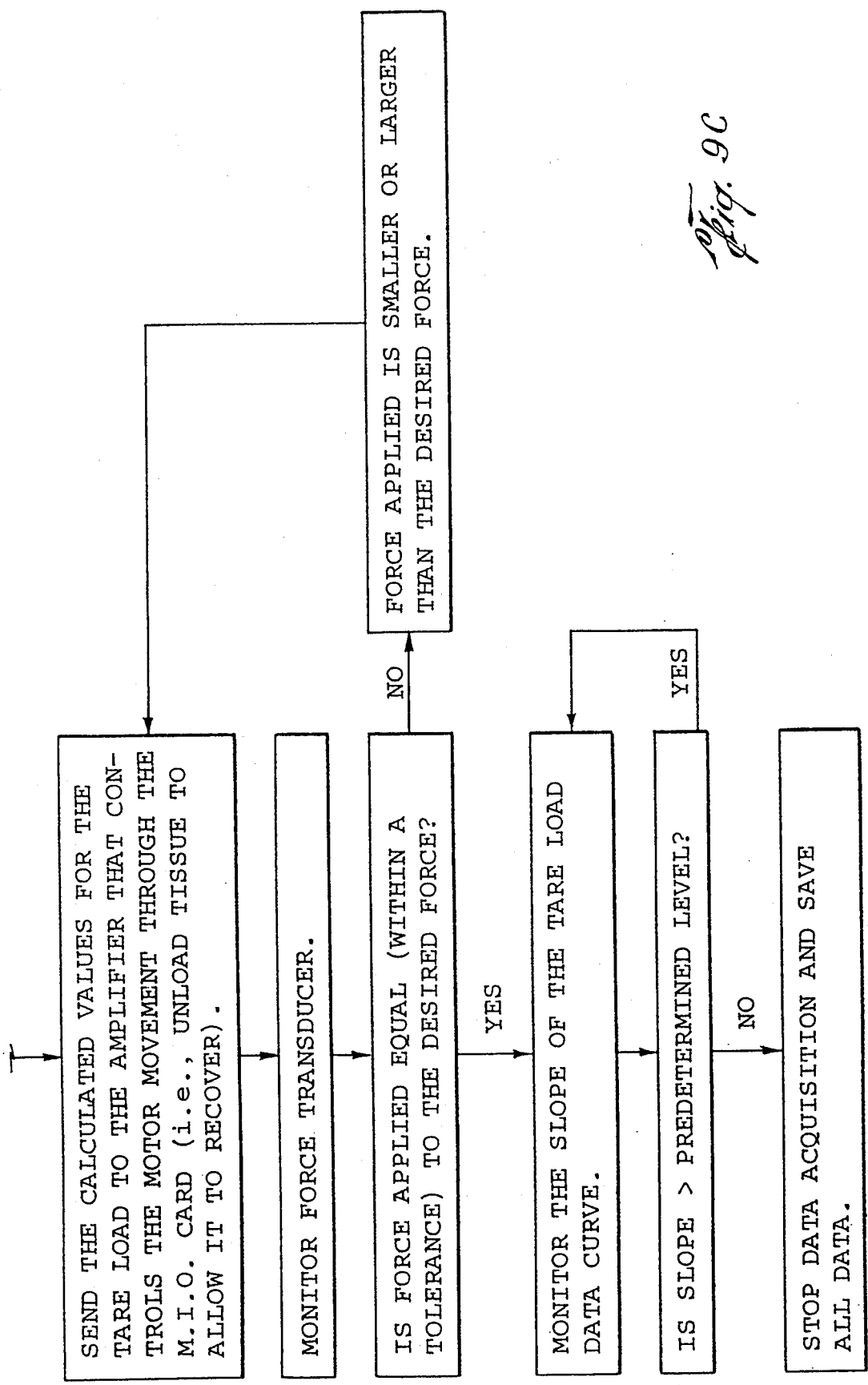

ARTHROSCOPIC INDENTER

This application is a continuation of application Ser. No. 07/871,523, filed Apr. 21, 1992, now abandoned.

BACKGROUND OF THE INVENTION

1. Field of the Invention

The present invention relates to an arthroscopic indenter in general and, more particularly, to an apparatus and method for measuring internal properties of cartilage.

2. Description of the Relevant Art

The effects of articular cartilage degenerative diseases (such as osteoarthritis or chondromalacia patella) are visible to the naked eye when the disease has reached an advanced stage. Manifestations of these diseases include changes in the tissue's: 1) biomechanical properties (stiffness, permeability, compressibility), 2) biochemical composition (type II collagen, proteoglycan macromolecules, interstitial water content), and 3) morphological characteristics (surface fibrillation and fraying, osteophyte formation). At the early stages of cartilage degeneration, the tissues's stiffness decreases and its compressibility and permeability increase. Thus, a reliable means to quantify the initial stages of cartilage degeneration is to obtain its mechanical (or material) properties. This can be accomplished during arthroscopy, which is an in vivo and in situ procedure, using a probe to examine qualitatively the articular surfaces. Using direct vision provided by an arthroscopic fiberoptic tube connected to a videocamera, the probe is used to palpate the tissue and, based on the tissue's indentation, the orthopaedist decides on the existence or severity of the disease. During this procedure, the orthopaedist also examines visually the surface characteristics of cartilage. This procedure is neither objective nor successful in determining the early stages of degenerative diseases, during which visual abnormalities are not present.

A device used to measure the "deformation resistance" of tissue, and particularly the articular surface of the patella, is described in U.S. Pat. No. 4,364,399. This arthroscopic instrument simply measures the amount of resistance pressure exerted by the cartilage at a given indentation. Positioning of the probe is manually accomplished, and perpendicularity of the probe relative to the cartilage surface is subjectively determined. The distance of indentation is mechanically calculated often using manual placement of the pressure transducer against the cartilage surface. Manual indentation process is not sufficiently accurate to allow repeatable, objective measurements. Manual indentation devices cannot programmably vary the applied indentations or forces in order to more accurately obtain mechanical characteristics of the cartilage. This device does not measure the thickness of articular cartilage. Two tissues with the same mechanical properties but unequal thicknesses will exhibit different deformation or force resistance. Thus, the thickness of the tissue must also be measured and used to normalize the measured tissue deformation or force resistance. Furthermore, the device of U.S. Pat. No. 4,364,399 is used to apply indentations onto cartilage without immobilizing the cartilage's subchondral bone relative to the device. Thus, under indentation, not only cartilage but other surrounding or underlying soft tissues deform. As a result, when both the cartilage and surrounding tissue deform, the applied cartilage indentation is not accurately known, and the measured cartilage resistance may be irrelevant. Thus, manual indentation devices provide an extremely subjective value of the tissue's deformation and force behaviors.

While indentation techniques are preferable over arthroscopic observations, manual indentation techniques do not provide sufficient data to allow accurate and repeatable internal mechanical measurements to be taken of the cartilage.

SUMMARY OF THE INVENTION

The problems outlined above are in large part solved by the apparatus and method of the present invention. That is, the arthroscopic indenter hereof utilizes high resolution displacements or loading forces placed substantially perpendicular upon the cartilage via a loading shaft having an indenter tip. Specifically, applied or resistive forces and applied or developing displacements are measured, recorded, and fed back upon the indenter tip using a closed-loop computer feedback system. The computer controlled indenter with feedback can more accurately and repeatably measure the internal characteristics of cartilage using creep deformation and/or stress relaxation techniques described below.

As used herein, "creep deformation" is defined as the method by which a constant force is applied to the cartilage surface via the indenter tip and resulting cartilage displacement under the tip is measured as a function of time. The constant applied force, the ensuing displacement profile and the tissue thickness can then be used to compute intrinsic mechanical properties of the cartilage. In addition, "stress relaxation" is defined as the technique by which a constant displacement distance is applied to the tissue via the indenter and resulting force equilibrium is measured. The constant applied displacement, the corresponding force resistance profile and the cartilage thickness can also be used to compute the intrinsic properties of the cartilage. Either creep deformation or stress relaxation techniques can produce an accurate measure of the intrinsic mechanical characteristics of the cartilage such as compressive stiffness (aggregate modulus), apparent compressibility (Poisson's ratio) and permeability. Stiffness, compressibility and permeability are three important factors used in predicting the location and amount of the degenerative disease existing in cartilage.

Broadly speaking, the present invention contemplates an arthroscopic indenter for measuring the creep deformation profile and/or the stress relaxation profile of cartilage. The apparatus includes a loading shaft having a proximal end and a distal end. The distal end can be placed proximate to cartilage to be measured. An electromechanical actuator capable of axially moving the shaft in response to electrical input, is attached to or near the proximal end of the shaft. The actuator may include a motor and a cam used to axially displace the distal end at a constant force upon the cartilage. To measure creep deformation, a computer is used to programmably command the motor to apply constant force and it also records the amount by which the distal end displaces the cartilage while maintaining constant force upon the cartilage. Alternatively, to measure stress relaxation the computer commands the motor to measurably force the distal end at a set displacement upon the cartilage. The computer also records the resistive force exerted by the cartilage upon the distal end at the set displacement distance.

This invention further comprises a system for aligning the loading shaft. The system includes a frame positioned proximate to the cartilage and a protective sheath attached to the frame. The protective sheath includes a distal tip which can be securably positioned substantially perpendicular to the surface of the cartilage. The loading shaft may then be slidably placed within the sheath, whereby the distal end of the loading shaft is then placed in substantially perpendicular contact with the cartilage.

The present invention also contemplates an apparatus for closed-loop controlling creep deformation and stress relaxation tests performed on cartilage. The apparatus includes a loading shaft having a proximal end and a distal end, wherein the distal end is placed substantially perpendicular to or near cartilage to be measured. A motor may be attached to the proximal end to extend the distal end upon the cartilage, and a computer is adapted to monitor equilibrium readings of said cartilage by actuating the motor a set distance in accordance with closed-loop input sent from the proximal end to the computer.

According to one aspect of the apparatus for closed-loop controlling creep deformation and stress relaxation, a force transducer is attached to the loading shaft to measure force applied to the cartilage by the loading shaft or the resistive force applied by cartilage against the shaft. A position detector is also coupled to the loading shaft to measure the distance by which the distal end extends upon the cartilage. The computer operates on a closed loop principle by receiving input from the force transducer and position detector, and then outputting programmed electrical signals to the motor in accordance with the input.

The present invention also contemplates a method for determining substantially perpendicular placement of an arthroscopically placed loading shaft upon the outer surface of the cartilage. The method includes fixing a frame proximate an articular joint and movably securing a protective sheath to the frame. A light transmitter and at least one light receiver can be slidably placed into the protective sheath to direct a light beam at the surface of the cartilage and then detect light reflected from the surface. The protective sheath is then secured to the frame when the detected light received upon the receiver is at a maximum, thus indicating perpendicularity.

The present invention also contemplates a method for determining internal equilibrium properties of cartilage. The method includes positioning the distal end of a loading shaft through skin substantially perpendicular to underlying cartilage. The distal end is then measurably extended upon said cartilage at a measurable force, wherein internal equilibrium properties can be calculated from measuring the force and the distance by which the distal end extends upon the cartilage.

BRIEF DESCRIPTION OF DRAWINGS

Other objects and advantages of the invention will become apparent upon reading the following detailed description and upon reference to the accompanying drawings in which:

FIG. 1 is a perspective view of an alignment system for aligning a loading shaft according to the present invention;

FIG. 2 is a cross-sectional view along plane 2—2 of FIG. 1;

FIG. 3 is a perspective view of the alignment system utilizing a fiber optic alignment arrangement according to the present invention;

FIG. 4 is a perspective view of an apparatus for determining mechanical properties of cartilage according to the present invention;

FIG. 5 is a detail view of section 5 of FIG. 4;

Figure 6A:
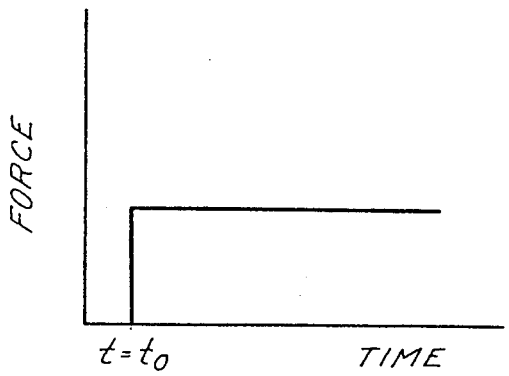
FIGS. 6A and 6 are graphs showing creep deformation at constant force achievable by the present invention.

While the invention is susceptible to various modifications and alternative forms, the specific embodiments thereof have been shown by way example in the drawings and will herein be described in detail. It should be understood, however, that the drawings are not intended to limit the invention to the particular form disclosed, but on the contrary, the intention is to cover all modifications, equivalence and alternatives falling within the spirit and scope of the invention as defined by the appended claims.

DETAILED DESCRIPTION OF THE INVENTION

Turning now to the drawings, FIG. 1 illustrates an alignment system 10 affixed to, for example, diarthrodial joint 12. Joint 12 includes skin 14 placed over a soft tissue 16, cartilage 18 and bone 20. Without limiting the scope of the present invention, cartilage 18 as well as any form of hard or soft tissue can be mechanically characterized by the present invention.

Alignment system 10 is mounted on joint 12 using at least two thumb screws 22 as shown in FIG. 1. Screws 22 preferably extend through skin 14 and rigidly attach to bone 20 at the distal tip of each screw 22. Bone 20 provides a rigid foundation upon which frame 24 can be securably fixed. Thus, during use, frame 24, screw 22 and bone 20 remain in fixed relationship to each other.

Housing 26 is fixed at one end of frame 24 by a suitable machine bolt 28 placed through housing 26 and into frame 24° Confined between bolts 28 and within housing 26 is a moveable plate 30. Plate 30 has two opposing planar surfaces upon which a ball socket clamp set 32 is affixed substantially near the center of one plane. Plate 30 and attached clamp set 32 are moveable in two dimensions (i.e., along the x and y axes) by removing the tension between the pad 34 and plate 30. Once the desired x and y position is determined, thumb screws 35 are tightened causing plate 30 to be drawn tightly between housing 26 and pads 34.

Clamp set 32 as well as plate 30 and housing 26 all have an opening or port through which a protective sheath 36 can be placed. Clamp set 32 with ball-and-socket reciprocation allows sheath 36 to be tilted in a variety of angles with respect to frame 24. Once a desired angular tilt is established, a first locking thumb screw 38 can be tightened, thus fixing sheath 36 at the desired angular position. Moreover, sheath 36 can be moved along an axis substantially perpendicular to the plane formed by the x and y axes (i.e., along the z axis) by displacing sheath 36 within the passage formed through clamp set 32, plate 30 and housing 26. Once the proper z displacement is achieved, second locking thumb screw 40 can be tightened thereby affixing sheath 36 to clamp set 32.

Sheath 36 is tubular in shape and can be of varying geometry. A suitable geometry is a length of approximately 15 cm with a 4.6 mm outside diameter. Sheath 36 is made of any form of rigid material including but not limited to surgical quality stainless steel, titanium-base alloys, or cobalt-base alloys. A nominal inside diameter of sheath 36 may be approximately 4.2 mm to accommodate an alignment shaft 42.

As shown in FIG. 2, alignment shaft 42 is a cylindrical body that encapsulates a fiber optic cable 44 through which a light source can pass. At least one receiver 46 can be arranged at a radially spaced distance from cable 44. Receiver 46 may include either a fiber optic cable arranged substantially parallel to cable 44 for receiving reflected light or a photodiode arranged at the distal tip of shaft 42 for converting reflected light to electrical signal.

As shown in FIG. 3, the distal tip of alignment shaft 42 can be placed proximate to the outer surface of cartilage 18 but spaced a small distance therefrom. The distal end of alignment shaft 42 is inserted through an incision of approximately 5 mm length formed in skin 14. A 5 mm incision is a typical incision geometry used in normal arthroscopy. The distal end follows the insertion down to the point of interest proximate to cartilage 18. Alignment shaft 42 is then locked in place relative to sheath 36 with a thumb screw 47. It is of primary importance that alignment system 10 be used to align protective sheath 36 in a substantially perpendicular orientation to cartilage 18 residing directly beneath sheath 36. Accordingly, alignment shaft 42, carrying fiber optic cable 44 and receivers 46, is used to align sheath 36 in a substantially perpendicular orientation. Namely, alignment is achieved by transmitting light waves through fiber optic cable 44 to illuminate a circular area upon cartilage 18. The area is approximately 2.0 mm in diameter and indicates the transmitted light waves striking cartilage 18 and reflecting therefrom. The reflected waves are detected as they strike receivers 46 placed radially around cable 44. Alignment shaft 42 is tilted via clamp set 32 and/or translated in the x or y axes via moveable plate 30 until the transmitted light waves reflect directly back onto receivers 46 from a substantially perpendicularly arranged portion of the surface of cartilage 18. This occurs when receivers 46 sense maximum detected quantity of light waves. Instead of only one or two radially spaced receivers detecting light (indicating a tilt condition), all detectors receive a maximum amount of light of somewhat equal magnitude. When receivers 46 receive maximum reflected light, indicator 48 produces a visual light 50 or an audible alarm 52.

Receivers 46 may be either fiber optic cables for receiving reflected light or photodiodes (preferably PIN photodiodes) for converting reflected light to electrical signals which are then transmitted through shaft 42 to indicator 48. Either form of detector may be used.

A suitable alignment shaft including fiber optic cable 44, receivers 46 and indicator 48 is produced by Keyence Corp. of America, Fair Lawn, N.J. as Model No. FS2-60.

Once protective sheath 36 is securably positioned substantially perpendicular to a portion of the surface of cartilage 18 directly beneath sheath 36, alignment shaft 42 can be removed from the sheath 36. An appreciable advantage of the present invention is the various degrees of movement and rotation which can be adjustably applied upon sheath 36. Once the desired position is detected convenient thumb screws 35, 38, 40 can be tightened to fix the relative position of sheath 36 in relation to cartilage 18. Sheath 36 thereby provides a positioning passage way into which loading shaft 54 can be placed as shown in FIG. 4. Coupled to one end of loading shaft 54 is a servo motor assembly 56. Unislide assembly 57 functions to allow coupler 60 and attached hardware to slide upon servo motor assembly 56. Coupler 60 is used for attaching an electromechanical actuator or motor 62, with an axially moveable shaft, to positional detector 64.

Loading shaft 54 is preferably made of stainless steel with approximately 2.0 mm outside diameter with a sintered steel porous indenter tip 66 placed at the distal end of loading shaft 54. Housing 58 and the base of servo motor assembly 56 are made of any form of rigid material such as, for example, stainless steel or aluminum. A suitable servo motor may be obtained from Northern Magnetics, Inc. Model No. ML2-1005-007JBT having a stroke of 12.7 mm and a maximum continuous force of 3.12N and continuous power of 4.5 Watts. A suitable servo motor assembly 56 may be obtained from Velmex, Inc. Model No. A1503K2-S1.5 with a maximum unislide travel distance of 38.1 mm and having lead screw 68 transverse movement of 1 cm per 5 turns. Still further, a suitable positional detector 64 is a linear variable differential transformer (LVDT) manufactured by Trans-Tek, Inc. Model No. 0242-0000 A-91 having a range of approximately ±6.35 mm with an excitation voltage of 6 volts DC to 30 volts DC. Positional detector 64 produces an analog output 69 signifying the relative position of loading shaft 54. The analog output 69 is of substantially infinite resolution.

Also attached between motor 62 and shaft 54, at the proximal end of shaft 54, is a force transducer 70 adapted to measure the amount of force applied to cartilage 18 by loading shaft 54. Conversely transducer 70 can measure the resistive force applied to shaft 54 by internal mechanical resilience of cartilage 18. Force transducer 70 may be obtained from Transducer Techniques, Inc. Model No. MDB-5 having a range of −22.3N (compression) to ±22.3N (tension). Excitation voltage upon Model No. MDB-5 is approximately 10 volts DC having an electrical analog output 72, which is substantially infinite in resolution.

Once loading shaft 54 is inserted into sheath 36 and locked into place with sheath lock 74, unislide housing 58 and the outer housing of positional detector 64 are rigidly attached to each other. Motor 62, force transducer 70, inside moveable core of positional detector 64 and loading shaft 54 (with indenter tip 66) are fixed in position relative to each other and move as a unit. As a result, the unislide lead screw 68 controls the position of indenter tip 66 relative to cartilage surface 18. Indenter tip is translated with unislide lead screw 68 to close proximity to the surface of cartilage 18. Indenter 66 will then be used in both creep deformation testing and stress relaxation testing to determine the intrinsic mechanical properties of cartilage 18.

Creep deformation testing begins by utilizing a computer 76 with feedback closed-loop control, which sends an analog signal 77 via amplifier 80 to motor 62. By way of example, computer 76 receives programmed input to apply a load force (e.g., 0.0687N tare load) via a 2.0 mm diameter flat-ended cylindrical, rigid, porous indenter tip 66. The loading tare force is delivered by output signal 77 sent from computer 76 to motor 62. The tare force remains constant and is used to allow the operator to establish a reliable starting level (or zero position) of the tissue's surface. As the cartilage surface 18 deforms, the positional detector 64 core moves relative to the outer housing of detector 64 and produces an analog signal 69 (voltage) which is linearly related to the amount of displacement recorded by detector 64. The slope of the tare load creep is monitored by the computer and when the slope becomes smaller than a preprogrammed amount (e.g., $1 \times 10^{-6}$ mm/s) computer 76 sends a new signal output 77 through amplifier 80 to motor 62. Motor 62 then reciprocates by increasing the force upon cartilage 18 via indenter tip 66. The increased load (e.g. 0.438N) is used to further deform cartilage 18 caused by axial movement of tip 66.

Creep deformation is the deformation of cartilage 18 as a function of time in response to a constant force or load placed upon cartilage 18. Positional detector 64 output is collected by computer 76 via multi-input/output card (National Instruments, Model No. NB-MIO-16XL-42) within computer 76 (not shown). Multi-input/output card receives analog input 69 from detector 64. Data points are then collected and plotted on the screen every 2.5 μm of deformation-change or every 100 seconds, whichever happens first, for ten minutes. At the end of ten minutes, the test load is removed and cartilage 18 is allowed to recover for approximately 8 minutes at which time data acquisition ceases automatically as determined by program input within computer 76.

Figure 6B:
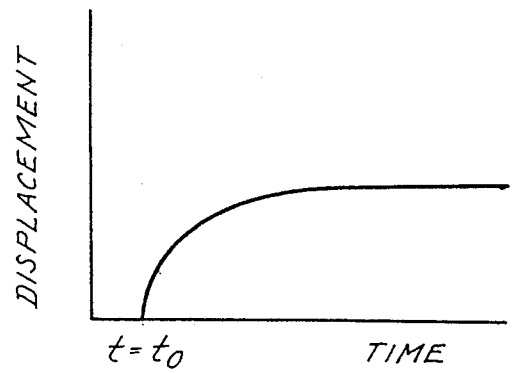

FIG. 6A is a graph illustrating the constant force applied by the indention tip. FIG. 6B shows a typical, corresponding, cartilage deformation profile as a function of time. Creep deformation equilibrium is particularly suited for measuring intrinsic mechanical properties of cartilage 18 such as, e.g. compressibility, stiffness and permeability.

Figure 7A:
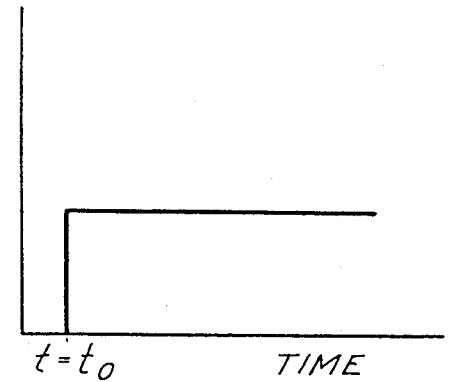
FIGS. 7A and 7B are graphs showing stress relaxation at constant displacement achievable by the present invention.
Figure 7B:
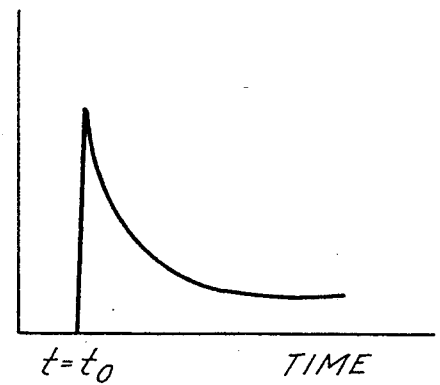

Similar to creep deformation equilibrium technique described above, stress relaxation equilibrium utilizes the same apparatus while applying a different programmed technique. Instead of applying a constant force and measuring the resulting displacement, stress relaxation applies a set displacement upon indenter 66 and measures the resulting resistive force exerted by cartilage 18 upon tip 66 as shown in FIGS. 7A and 7B. Stress relaxation technique utilizes an initial displacement of, e.g., 10 μm applied substantially perpendicular to cartilage 18 by motor 62 to begin data acquisition of resistive force. The slope of this resistive force is calculated and when it becomes sufficiently small (e.g., $1 \times 10^{-6}$ N/s), computer 76 sends new output voltage 77 through amplifier 80 to motor 62 which corresponds to maximum force of approximately 3.12N. The objective is to achieve a constant cartilage displacement (step displacement) of, e.g., 0.2 mm under indenter tip 66. Positional detector output 69 is monitored until the desired step displacement of, e.g., 0.2 mm is achieved, while force transducer 70 measures the reaction or resistive force developed by cartilage 18 as a response to the applied step displacement. This resistive force is expected to increase very fast as a function of time to the applied step displacement as shown in FIGS. 7A and 7B. Thereafter, resistive force will decrease or "relax" to an equilibrium point as shown in FIG. 7B.

Stress relaxation, creep deformation, and thickness provide inputs by which intrinsic material properties of cartilage 18 can be obtained. Such properties include, but are not limited to, compressive stiffness, apparent compressibility and permeability. Permeability is the degree of difficulty of cartilage 18 interstitial fluid to move in and out of extracellular solid matrix or collagen material. Thus, arthroscopic indenter 66 can be used as either a prognostic or diagnostic tool useable in orthopaedics by obtaining variations in intrinsic mechanical properties of cartilage in a joint. An orthopaedic physician can thereby use the present apparatus to identify areas with potential for degeneration. This information will help the physician suggest changes in physical activities and exercise, and design surgical strategies which can alleviate mechanical stresses in these subject areas. Thus, the process of degenerative disease may be curbed.

Figure 8:
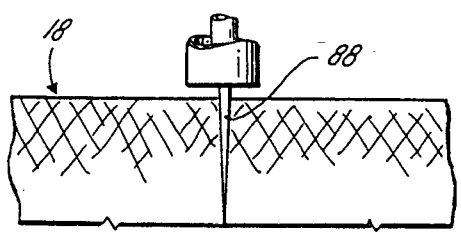
FIG. 8 is a detail view showing a needle thickness probe placed at the distal end of the loading shaft.

An additional variable used in obtaining intrinsic properties using the device hereof includes measurement of cartilage thickness at the test site. Indenter tip 66 can be replaced with a needle thickness probe 88 having a substantially smaller outside diameter than, for example, the 2.0 mm diameter indenter tip 66. An exemplary needle 88 is illustrated in FIG. 8 having a nominal diameter of approximately 0.1 mm.

To measure thickness of cartilage 18, motor 62 is instructed by computer 76, to move needle 88, until needle 88 encounters a larger resistive force provided through contact with cartilage. The needle translates through cartilage until a sudden increase in resistive force, e.g., 3N, indicates the needle's contact with underlying denser material such as bone. As needle 88 moves, its position is monitored with positional detector 64. Thus, at each instant both the resistive force of needle 88 and its position are simultaneously recorded by computer 76 until resistive or resultant force reaches 3N. When needle 88 travels through air, it encounters no appreciable resistance and the force is 0N. When the needle comes into contact with cartilage 18, a force gradient is registered by force transducer 70. When the needle encounters the calcified portion of cartilage 18 lying within deep zone of the cartilage or when needle 88 encounters bone 20, force transducer 70 signifies that it has traveled through the entire measurable cartilage layer. A second force gradient is observed by force transducer 70 which signifies this increase in resistive force.

Computer 76 operates as a processor which receives analog input 69 and 72, stores and/or processes that analog input, and sends a corresponding resultant output 77. Software may be programmed within computer 76 (e.g., a Macintosh IIcx, Apple Computer Inc., having 8 MB RAM) using an object-oriented programming language (e.g., Labview, National Instruments, Inc.). Analog output 77 from computer 76 can be amplified using amplifier 80. A suitable amplifier 80 may be obtained from Aeroteck, Inc. Model No. 3010-LS. Amplifier 80 can produce a continuous output current of up to approximately 3 amperes having a continuous power dissipation of 70 watts. A reproducible gain of 1.2 amps/volt is achievable over a bandwidth of 500 Hz using Model No. 3010-LS. Output from amplifier 80 is supplied to servo motor 62 as specified hereinabove.

Intrinsic mechanical characteristics of cartilage 18 are obtained from creep deformation techniques or stress relaxation techniques using, for example, a linear biphasic theory. Linear biphasic theory represents the mathematical algorithm by which three intrinsic mechanical properties of cartilage 18 (aggregate modulus, Poisson's ratio, and permeability) can be obtained using, for example, indentation creep or stress relaxation profiles. One particular methodology of linear biphasic theory used in determining intrinsic characteristics from creep deformation or stress relaxation is described in Mak A. F. et al., "Biphasic Indentation of Articular Cartilage—I. Theoretical Solution" *J. Biomech*, Vol 20, pp 703-714 (1987); Mow, V. C. et al., "Biphasic Indentation of Articular Cartilage—II. A Numerical Algorithm and Experimental Study, "*J. Biomech.*, Vol. 22, pp. 853-861 (1989). These references describe one of many theoretical principles and mathematical analyses used in obtaining intrinsic mechanical properties of cartilage. Any corresponding algorithm which utilizes stress relaxation and creep deformation data obtained hereinabove and then applies that data to achieve intrinsic mechanical characteristics, such as compressibility, stiffness and permeability, fall within the scope and spirit of this invention. While biphasic theory is certainly a plausible algorithm by which to obtain intrinsic properties of cartilage, any other methodology, including but not limited to elements or derivatives of the biphasic theory, may also be applied to obtain intrinsic properties using creep deformation or stress relaxation technique described hereinabove.

Figure 9A:
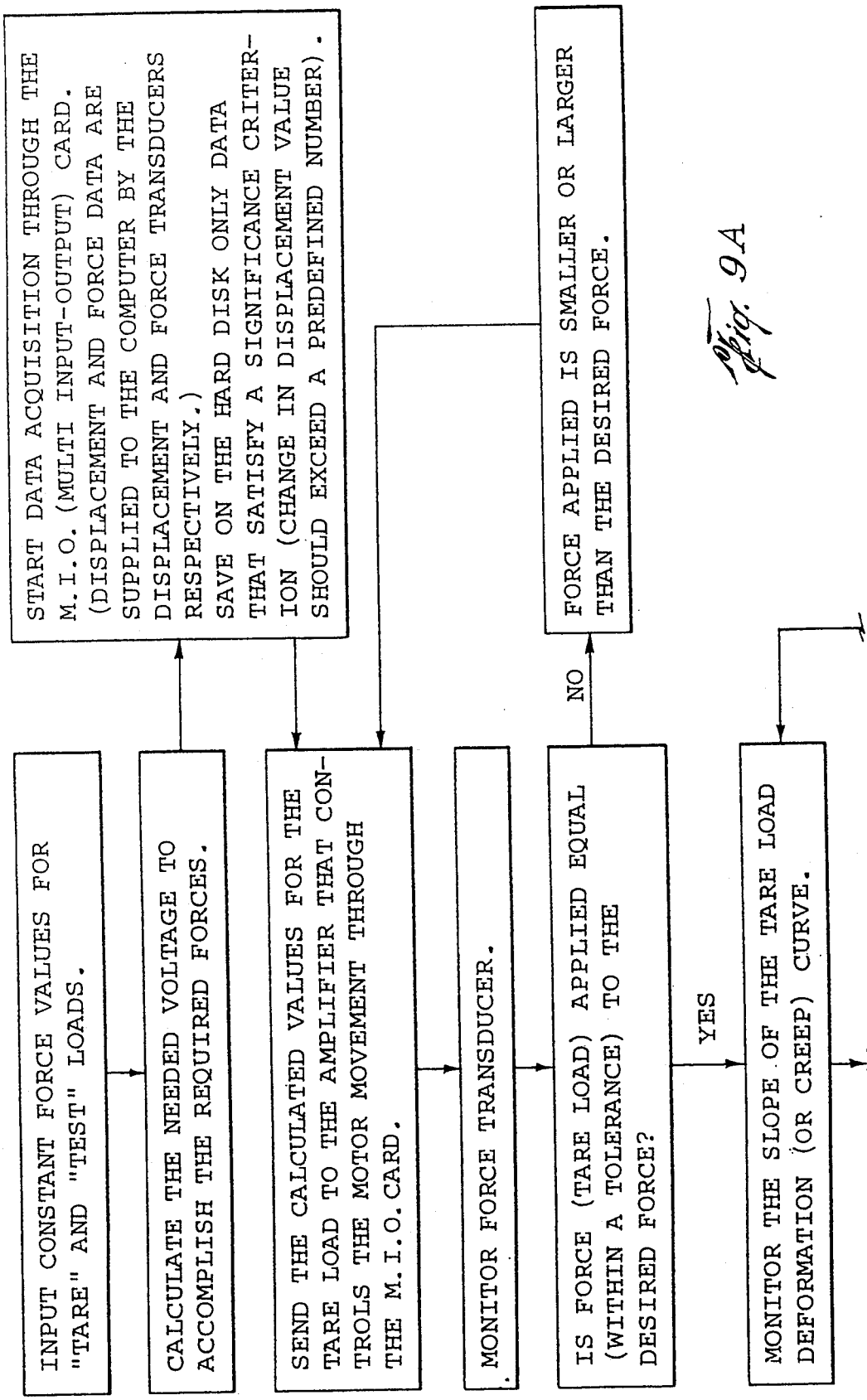
FIG. 9(A-C) is a flow diagram of steps used to perform creep deformation achievable by the present invention.
Figure 10A:
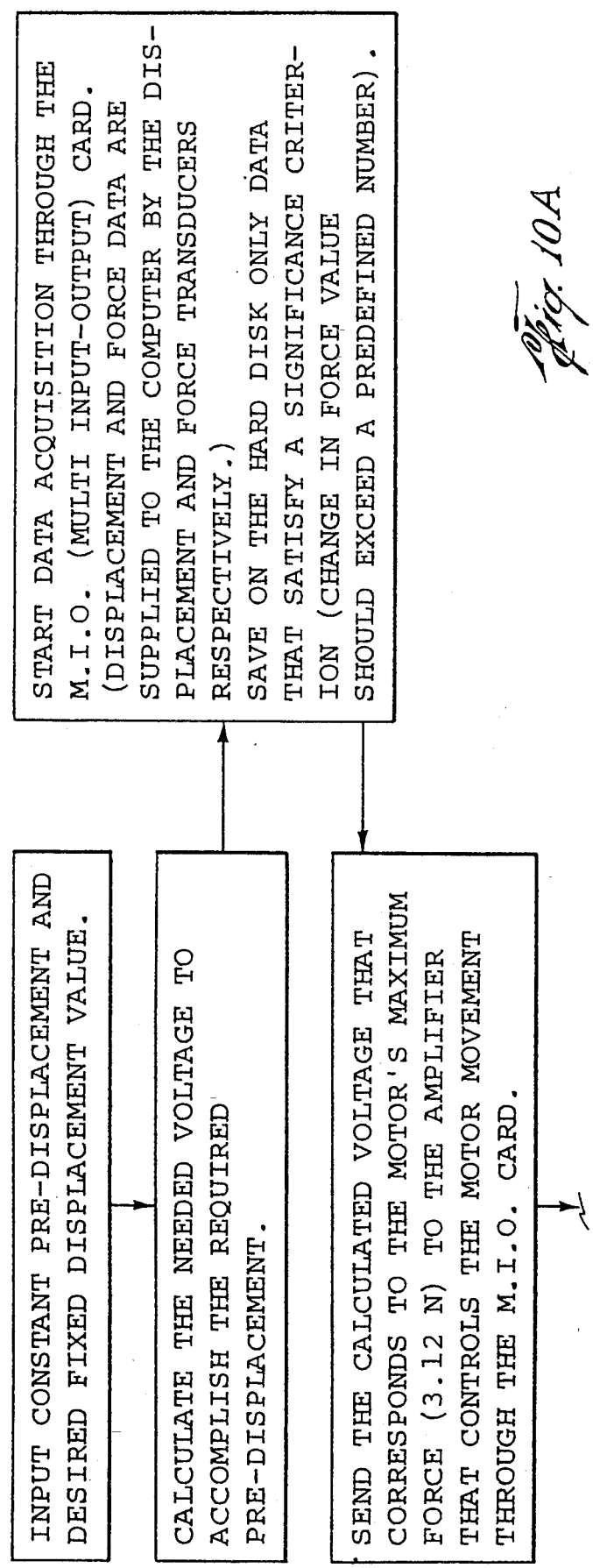
FIG. 10(A-C) is a flow diagram of steps used to perform stress relaxation achievable by the present invention.
Figure 10B:
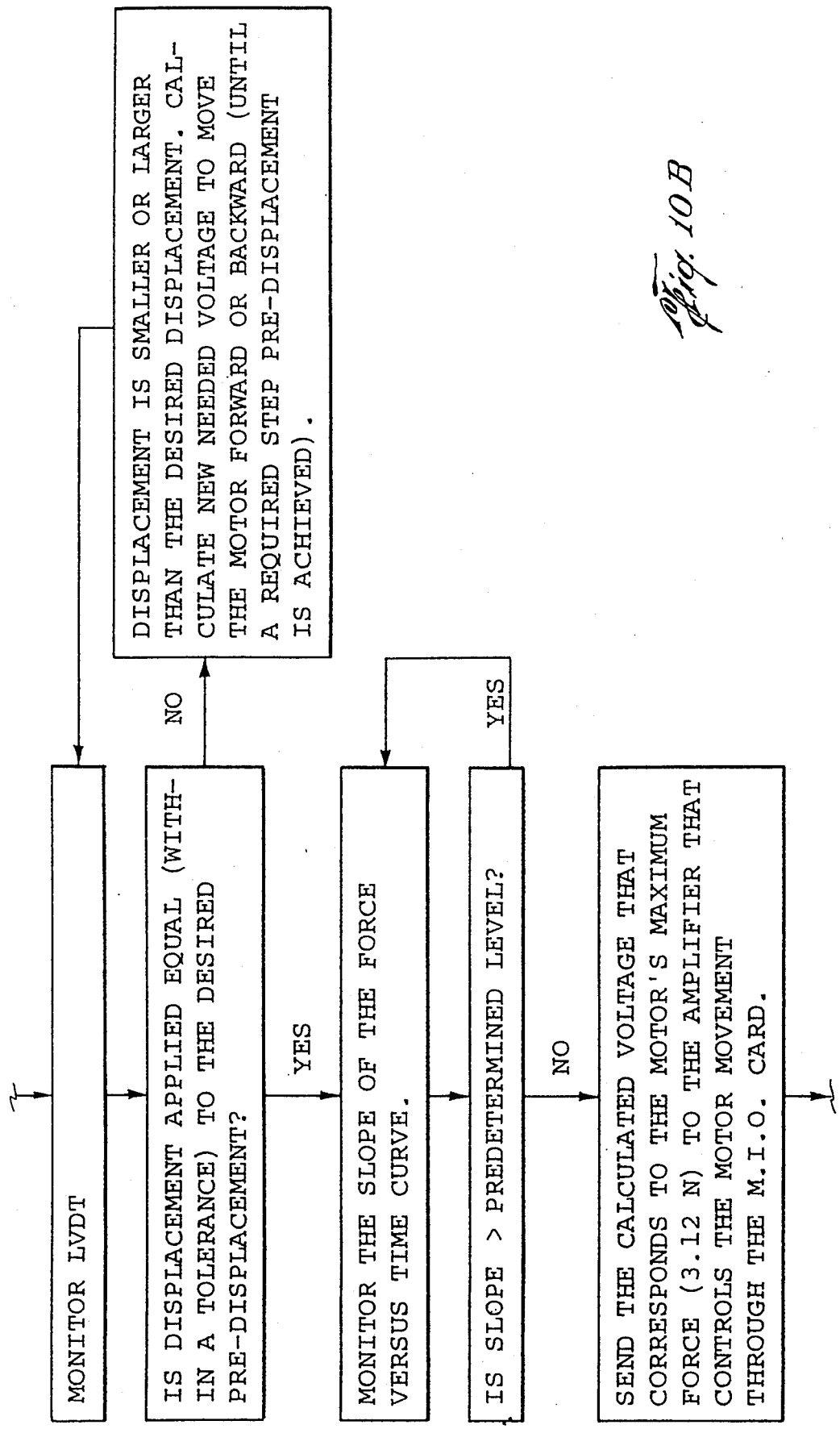
Figure 10C:
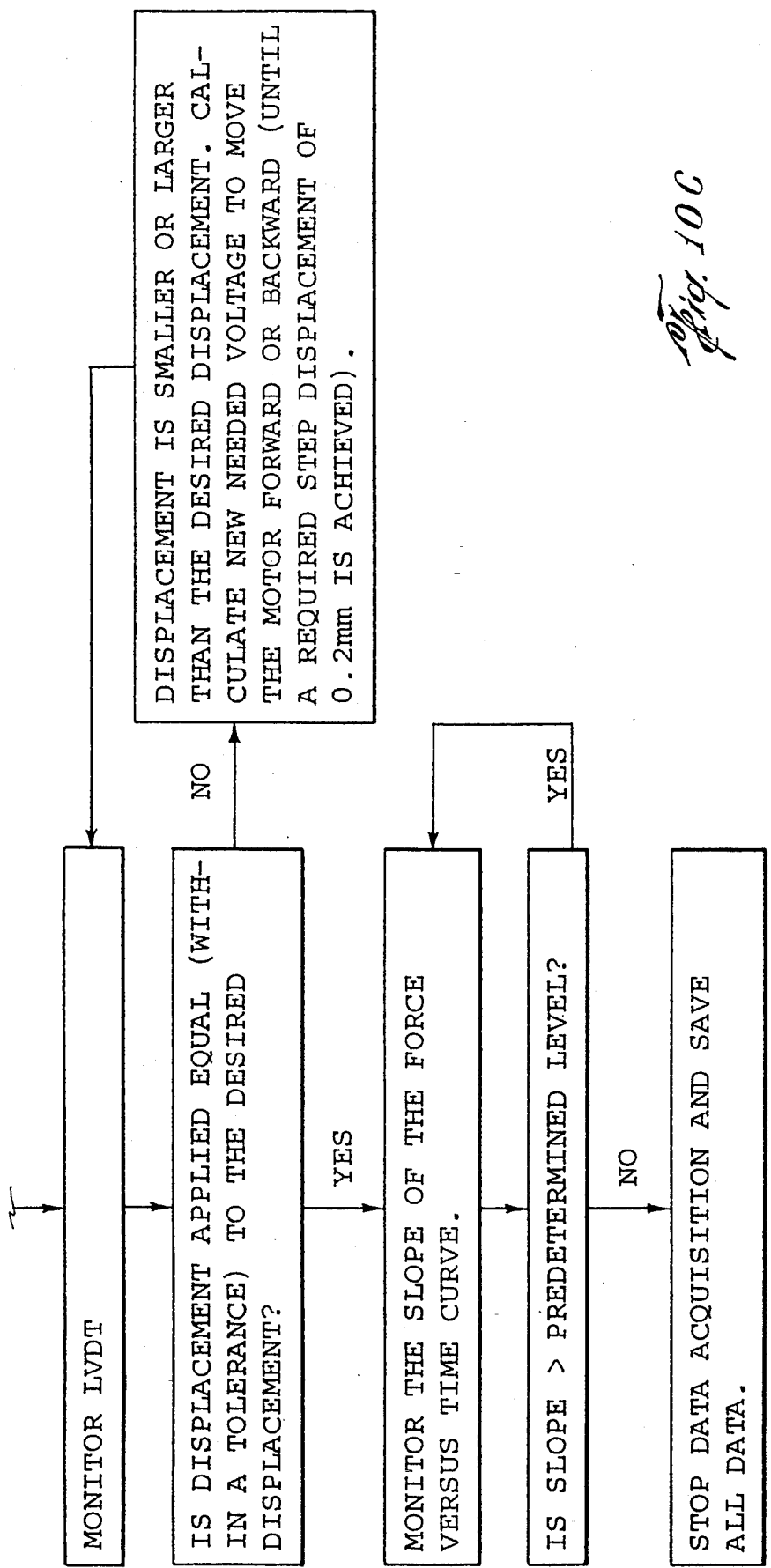
Figure 11:
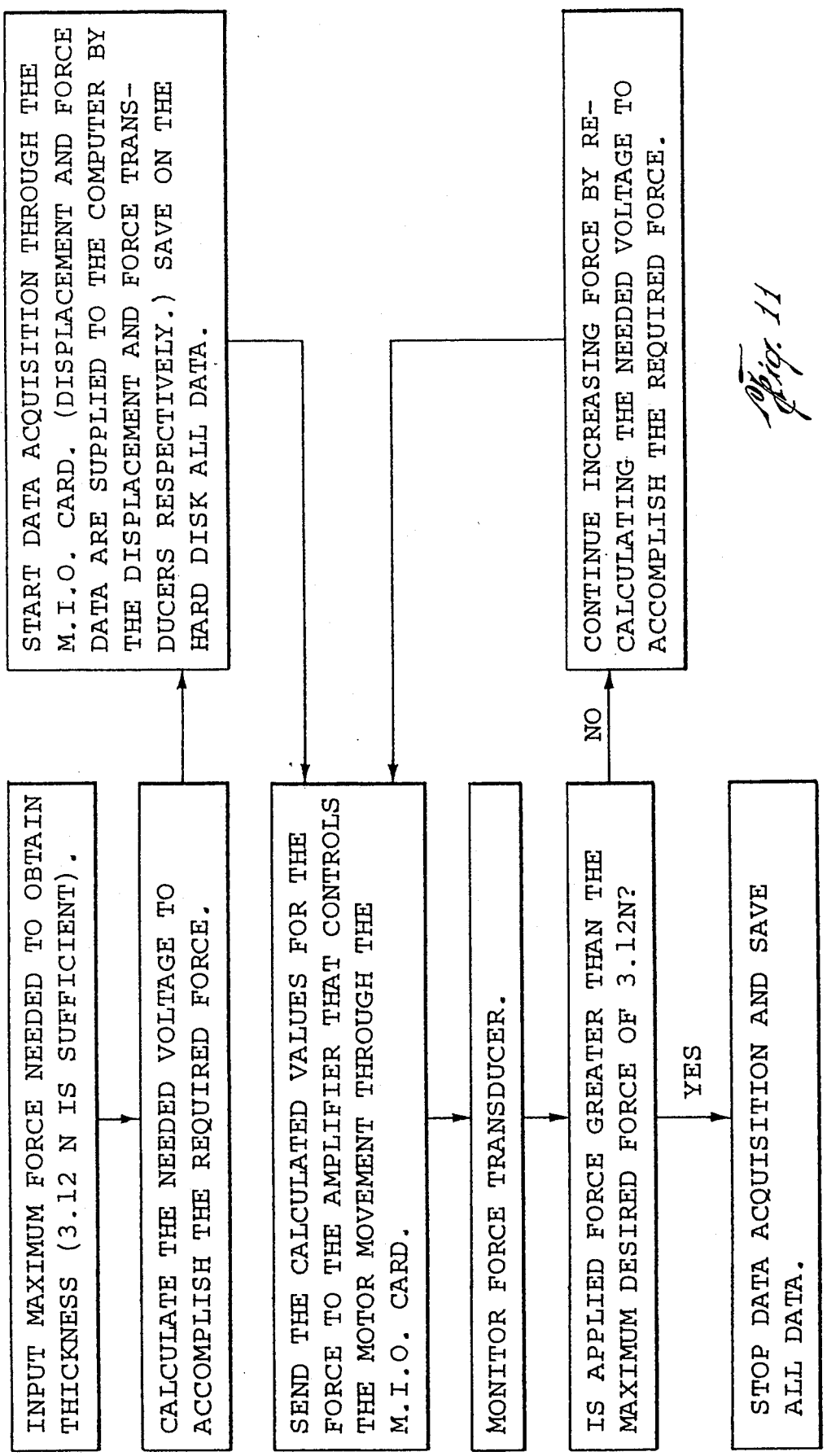
FIG. 11 is a flow diagram of steps used to perform thickness test achievable by the present invention.

Flow diagrams of various programming steps, capable of being input into computer 76, and necessary to achieve creep deformation, stress relaxation and thickness measurements are illustrated in FIGS. 9-11. Any suitable program language operable with computer 76 can be utilized to reconfigure the computer to achieve the necessary test steps.

As shown in FIG. 9, creep deformation includes numerous programmable steps beginning with both tare and test loads being input into computer 76. The tare and test loads are constant force values of which computer 76 will use to monitor deformational characteristics of cartilage 18. A multi-input/output (MIO) card associated with computer 76 controls and monitors both the tare and test loads applied to the indentor tip 66 of the present invention. The tare load is calculated in terms of voltage and sent to amplifier 80 which then controls movement of motor 62. The resulting force is monitored by force transducer 70. If the applied tare load is substantially equal to the desired force or load, then the slope of the tare load deformation or tare creep curve is monitored. If the slope of the tare creep curve is less than a predetermined level, then test operations can begin.

Creep deformation testing begins after tare loads are applied. Specifically, testing begins by sending calculated values for the test load to amplifier 80 which then controls motor 62. As stated above, tare load is generally less than test load and is used to initialize or set a bench mark for subsequent test readings. After the test load is applied via motor 62, force transducer 70 will monitor the resulting force to determine if the force applied, or test load, is substantially equal to the desired force. If test load is substantially equal to desired force, then the slope of the test load creep curve is monitored to determine if the slope is less than a predetermined level. Once the slope drops below the predetermined level, data acquisition and control stops and the experiment is finished.

Throughout the creep deformation process, a closed-loop system allows close monitoring of resultant force upon transducer 70 and readjustment of applied force sent by motor 62. The closed-loop system is controlled by programmed reconfiguration of computer 76. The software program necessary to achieve reconfiguration resides on hard disk of computer 76 or it can be stored on a portable memory medium such as a floppy disk, CD ROM, etc.

FIG. 10 illustrates the programmable steps used in achieving stress relaxation measurements by the system of the present invention. Similar to creep deformation, stress relaxation can measure the behavior of cartilage 18 in response to various displacement values exerted upon the cartilage. However, unlike the constant force values used in creep deformation, stress relaxation uses constant or fixed displacement values. In particular, stress relaxation requires a fixed displacement value be sent from computer 76 to motor 62. The desired voltage needed to accomplish the required pre-displacement is calculated and also sent to motor 62. If the resulting displacement is substantially equal to the desired pre-displacement, then the slope of the corresponding force is measured. Once the slope falls below predetermined level, the motor's maximum force is applied and the resulting displacement is monitored. If the resulting displacement being applied to the indenter tip is substantially equal to the desired displacement, then the time-line slope of the resulting force is determined such that once the slope is less than a predetermined level, data acquisition is discontinued and all data is stored within computer 76. Similar to creep deformation data, stress relaxation data can be saved and used immediately or at a later time.

FIG. 11 illustrates the steps used in measuring the thickness of cartilage 18. Generally, a maximum input force is applied via motor 62 to needle 88. As the needle translates, the resulting force measured by force transducer 70 is monitored by detector 64. Once the measured applied force becomes greater than the maximum desired force, then data acquisition will be discontinued and all data can be saved. Similar to creep deformation and stress relaxation measurements, thickness measurements utilize a closed-loop control of force and displacement using the programmable arthroscopic indenter of the present invention. However, instead of using an indenter tip, as is used in creep deformation and stress relaxation, thickness measurements require a small diameter needle 88 be substituted for the larger diameter indenter tip.

The foregoing description of the present invention has therefore been directed to particular preferred embodiments. It will be apparent, however, to those skilled in the art that modifications and changes in the various devices and methods described above may be made without departing from the scope and spirit of the invention. For example, any computer-based, closed-loop feedback system incorporating a motor, a positional detector, with or without a force transducer, may be made without departing from the scope and spirit of the invention regardless of how the various components are arranged or coupled to each other provided the resulting measurements are acquired using an automatic computer-based system. Therefore, equivalent elements may be substituted for those illustrated and described herein. Parts may be reversed, and certain features of the invention may be utilized independently of the use of other features, all as would be apparent to one skilled in the art after having benefited from the description of the invention. As can be appreciated from the above discussion, the invention can present a practical advance over conventional manual indenter devices which, by their nature, cannot achieve the level of accuracy obtained from the computer-based closed-loop system of the present invention.

What is claimed is:

1. A computer controlled indenter to measure stress relaxation of cartilage overlying bone comprising:
   a loading shaft having a distal end for placement proximate to the cartilage;
   a system for aligning the loading shaft comprising:
      a frame which can be fixed in relationship to the bone;
      a protective sheath for said loading shaft movably attached to said frame; and
      means for detecting reflected light for determining alignment of said sheath; and
      means for aligning said sheath substantially perpendicular to said cartilage;
   an electromechanical actuator comprising a motor and adapted to axially move said loading shaft;
   a force transducer adapted to measure a force applied to the cartilage by said loading shaft; and
   a computer, operatively connected to said actuator and transducer, to calculate stress relaxation of the cartilage as a function over time of measured force required to maintain said distal end at a set displacement upon the cartilage.

2. The indenter of claim 1 further comprising:
   (a) a needle thickness probe affixed to the distal end of the shaft; and
   (b) a computer adapted to calculate thickness of the cartilage during use as a function of displacement of the shaft between the point at which the measured force indicates the needle has encountered the cartilage and the point at which the measured force indicates the needle has encountered underlying bone.

3. The indenter of claim 1 wherein the force transducer comprises:
   (a) a surface placed in pressure communication with one end of the shaft; and
   (b) an electrical circuit attached to the surface, the circuit adapted to measure changes in electrical resistance in linear response to the force placed on the surface during use.

4. The indenter of claim 1 wherein:
   (a) said computer is adapted to establish and maintain a desired position for the shaft during a data-acquisition period; and
   (b) during the data-acquisition period, said computer is adapted to collect force versus time measurement data.

5. The indenter of claim 1 wherein:
   (a) said computer is adapted to establish a desired position of the shaft during a pre-data acquisition period; and
   (b) during the pre-data acquisition period, said computer is adapted to collect force versus time measurement data for determining the point for beginning the data acquisition period.

6. The indenter of claim 1 adapted to measure cartilage in vivo.

7. A computer controlled indenter to measure the creep deformation of cartilage overlying bone comprising:
   a loading shaft having a distal end for placement proximate to the cartilage;
   a system for aligning the loading shaft comprising:
      a frame which can be fixed in relationship to the bone;
      a protective sheath movably attached to said frame; and
      means for detecting reflected light for determining alignment of said sheath; and
      means for aligning said sheath substantially perpendicular to said cartilage;
   an electromechanical actuator comprising a motor and adapted to axially move said loading shaft while maintaining constant force upon the cartilage;
   a positional detector adapted to measure the displacement of said shaft; and
   a computer, operatively coupled to said actuator and said positional detector, to calculate creep deformation of the cartilage as a function over time of measured displacement of said shaft at a constant force applied to said loading shaft.

8. The indenter of claim 7 further comprising:
   (a) a needle thickness probe affixed to the distal end of the shaft; and
   (b) a computer adapted to calculate thickness of the cartilage during use as a function of displacement of the shaft between the point at which the measured force indicates the needle has encountered the cartilage and the point at which the measured force indicates the needle has encountered underlying bone.

9. The indenter of claim 7 wherein the position detector comprises a linear variable differential transformer having a displacement resolution.

10. The indenter of claim 7 wherein:
    (a) said computer is adapted to determine a zero position for the shaft at the cartilage tissue surface;
    (b) said computer is adapted to establish and control the actuator to maintain a predetermined force against the cartilage by the shaft during a data-acquisition period; and
    (c) during the data acquisition period, said computer is adapted to collect cartilage displacement versus time measurement data.

11. The indenter of claim 7 adapted to measure cartilage in vivo.

* * * * *